United States Patent
Rouyer et al.

(10) Patent No.: US 9,492,281 B2
(45) Date of Patent: Nov. 15, 2016

(54) ANKLE PROSTHESIS WITH SIMPLIFIED ADJUSTMENT

(75) Inventors: Guillaume Francois Antoine Rouyer, Fouesnant (FR); Damien Sandoz-Othenin, Miribel (FR)

(73) Assignee: European Foot Platform SC, Saint Louis (FR)

( * ) Notice: Subject to any disclaimer, the term of this patent is extended or adjusted under 35 U.S.C. 154(b) by 0 days.

(21) Appl. No.: 13/588,761

(22) Filed: Aug. 17, 2012

(65) Prior Publication Data

US 2013/0041473 A1 Feb. 14, 2013

Related U.S. Application Data

(63) Continuation of application No. PCT/IB2010/000622, filed on Feb. 19, 2010.

(51) Int. Cl.
*A61F 2/42* (2006.01)
*A61F 2/30* (2006.01)

(52) U.S. Cl.
CPC .... *A61F 2/4202* (2013.01); *A61F 2002/30387* (2013.01); *A61F 2002/30507* (2013.01); *A61F 2002/30538* (2013.01); *A61F 2002/30555* (2013.01); *A61F 2002/30578* (2013.01); *A61F 2002/4205* (2013.01); *A61F 2002/4207* (2013.01)

(58) Field of Classification Search
CPC ............ A61F 2/4202; A61F 2002/4205; A61F 2002/4207; A61F 2002/421
USPC ................ 623/20.32, 21.11, 21.18
See application file for complete search history.

(56) References Cited

U.S. PATENT DOCUMENTS

2004/0133282 A1* 7/2004 Deffenbaugh ........ A61F 2/4202 623/21.18
2008/0103603 A1* 5/2008 Hintermann ............... 623/20.32

FOREIGN PATENT DOCUMENTS

EP 1 435 222 A1 7/2004
WO WO 79/00739 A1 10/1979

OTHER PUBLICATIONS

International Search Report for Application Serial No. WO 2011/101699 dated Oct. 12, 2010.
European Application No. EP-10716617.5, Dec. 1, 2014 from EPO European Patent Office.

* cited by examiner

*Primary Examiner* — Brian Dukert
(74) *Attorney, Agent, or Firm* — Kenneth H. Sonnenfeld; Margaret B. Brivanlou; King & Spalding LLP

(57) ABSTRACT

The invention relates to an ankle prosthesis including a talar implant, a tibial implant, and an intermediate implant designed to be mounted to move relative to said talar implant in order to impart mobility to the ankle, said prosthesis further including embedded adjustment structure designed to alternate between a releasing state, in which they allow the intermediate implant to move relative to the tibial implant, and a locking state, in which they hold the prosthesis in the chosen assembly configuration, said prosthesis being characterized in that said adjustment structure can be controlled to be operable while the prosthesis is in the assembled state in vivo.

22 Claims, 2 Drawing Sheets

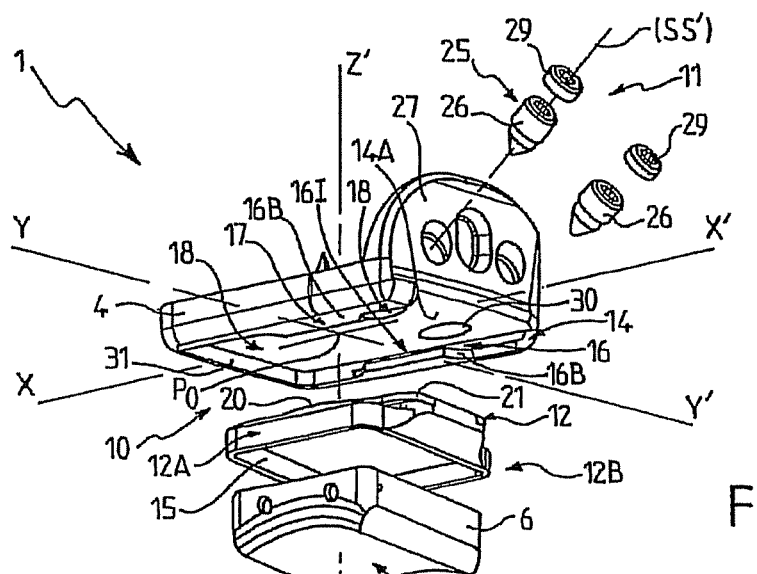
FIG.1
FIG.2
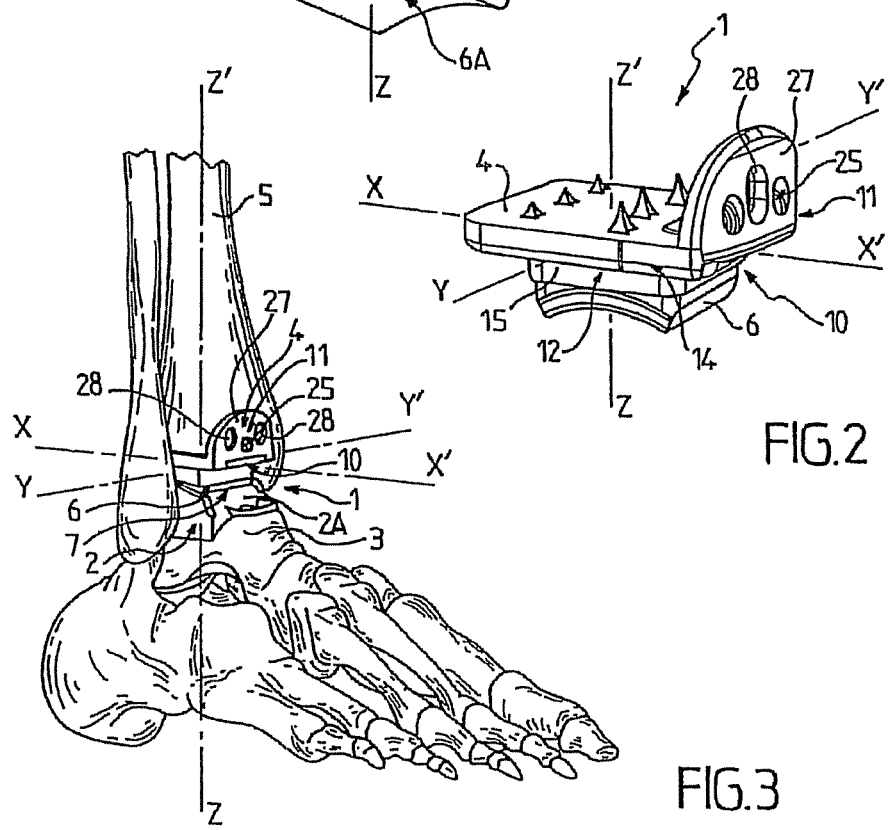
FIG.3

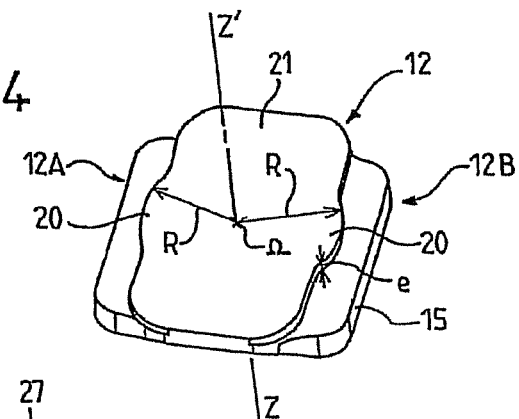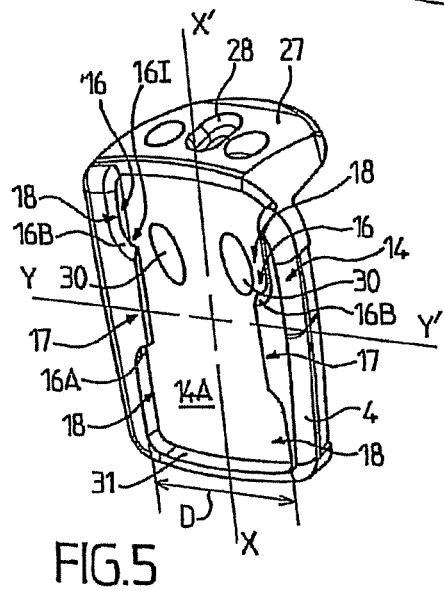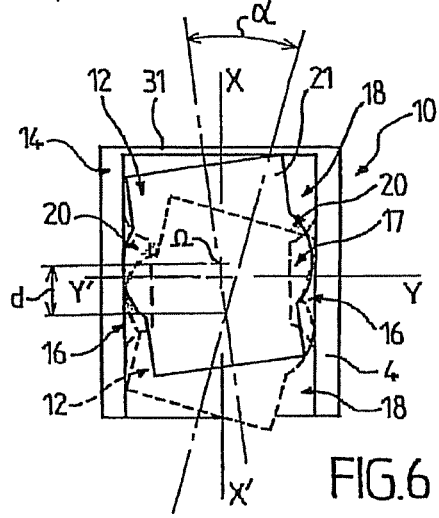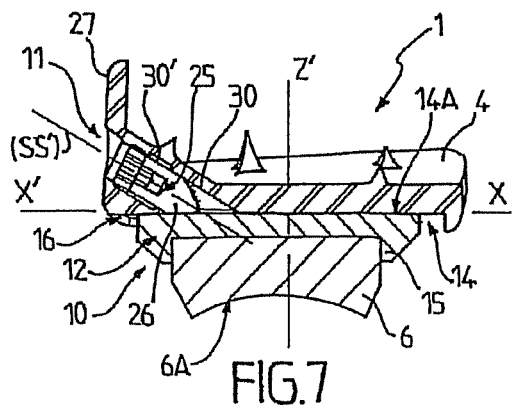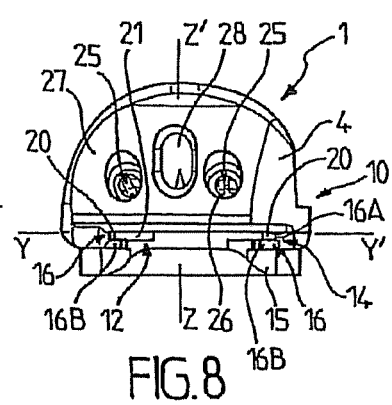

ANKLE PROSTHESIS WITH SIMPLIFIED ADJUSTMENT

CROSS-REFERENCE TO RELATED APPLICATION

This U.S. non-provisional patent application is a continuation of and claims priority to PCT Application No. PCT/IB2010/000622, filed on Feb. 19, 2010, the entirety of which is incorporated by reference herein.

TECHNICAL FIELD

The present invention relates to the technical field of joint prostheses, and more particularly to orthopedic implants making it possible to restore anatomical mobility to a joint, such as an ankle joint.

The present invention relates more specifically to an ankle prosthesis comprising a talar implant, a tibial implant, and an intermediate implant designed to be interposed between said tibial implant and said talar implant, said intermediate implant being designed to be mounted to move relative to said talar implant in order to impart mobility to the ankle, said prosthesis further comprising embedded adjustment means making it possible to modify the assembly configuration of the intermediate implant relative to the tibial implant, said adjustment means being designed to alternate between a releasing state, in which they allow the intermediate implant to move relative to the tibial implant with at least first and second degrees of freedom that are distinct from each other, and a locking state, in which they inhibit said first and second degrees of freedom so as to hold the prosthesis in the chosen assembly configuration.

BACKGROUND

It is known that ankle prostheses can be used to restore a certain amount of freedom of movement to an ankle joint, after the ankle has been damaged due to injury or to disease.

In particular, it is known that an ankle prosthesis can be implanted that comprises a talar implant, a tibial implant, and an intermediate implant interposed between said tibial implant and said talar implant for the purpose of imparting mobility to the ankle.

Depending on the treatment that is to be used on the patient, and also depending on the applicable regulatory requirements, it is possible either to allow the intermediate implant considerable freedom of movement relative to the tibial implant, e.g. by placing it in free planar abutment thereagainst, or, conversely, to hold said intermediate implant stationary against the tibial implant.

Unfortunately, restraining the intermediate implant relative to the tibial implant can cause considerable mechanical stresses to appear while the prosthesis is under load, in particular during walking, and such stresses can cause premature wear or indeed irreversible damage to the implants, or can cause discomfort to the patient.

That is why, in order to adapt such prostheses to match the anatomy of the treated patient, adjustment means have been devised for making it possible to modify the assembly configuration of the intermediate implant relative to the tibial implant.

Although such prostheses are generally satisfactory, they can however suffer from certain drawbacks.

The adjustment possibilities offered by prior art prostheses can be relatively limited, which does not always enable the overall arrangement of the prosthesis to coincide with the natural anatomy of the patient.

In addition, known adjustment methods generally use one or more test prostheses designed to enable measurements to be taken inside the patient's joint, those measurements then making it possible to configure the final prosthesis before said final prostheses is implanted.

Naturally, the use of such prior tests tends to increase the length of the surgical operation, and the trauma suffered by the patient, while also consuming a relatively large quantity of surgical equipment, and in particular a relatively large quantity of batches of test implants.

SUMMARY

Objects assigned to the present invention are therefore to remedy the above-mentioned drawbacks, and to provide a novel ankle prosthesis that is versatile, and that is capable of adapting to accommodate a very wide variety of therapeutic situations while also being particularly simple to implement.

Another object assigned to the invention is to provide a novel ankle prosthesis that is ergonomic and comfortable for the patient while it is being used.

Another object assigned to the invention is to provide a novel ankle prosthesis within which wear is minimized and that has increased longevity.

Another object assigned to the invention is to provide a novel ankle prosthesis that is of a design that is particularly simple and robust.

Another object assigned to the invention is to provide a novel ankle prosthesis that can be implemented in a manner that is particularly quick and intuitive.

Finally, another object assigned to the invention is to provide a novel ankle prosthesis that has good stability.

The objects of the invention are achieved by means of an ankle prosthesis comprising a talar implant, a tibial implant, and an intermediate implant designed to be interposed between said tibial implant and said talar implant, said intermediate implant being designed to be mounted to move relative to said talar implant in order to impart mobility to the ankle, said prosthesis further comprising embedded adjustment means making it possible to modify the assembly configuration of the intermediate implant relative to the tibial implant, said adjustment means being designed to alternate between a releasing state, in which they allow the intermediate implant to move relative to the tibial implant with at least first and second degrees of freedom that are distinct from each other, and a locking state, in which they inhibit said first and second degrees of freedom so as to hold the prosthesis in the chosen assembly configuration, said prosthesis being characterized in that said adjustment means are placed under the control of control means that are designed to be operable while the prosthesis is in the assembled state in vivo, so as to cause the adjustment means to alternate between their releasing state and their locking state.

BRIEF DESCRIPTION OF THE DRAWINGS

Other objects, characteristics, and advantages of the invention appear in-more-detail on reading the following description, and on examining the accompanying drawings, which are given merely by way of non-limiting illustration, and in which:

FIG. 1 is an exploded perspective view of a portion of a variant embodiment of an ankle prosthesis of the invention;

FIG. 2 is a perspective view of the elements of FIG. 1 in the assembled configuration;

FIG. 3 is a perspective view of a variant embodiment of an ankle prosthesis of the invention implanted in an ankle joint;

FIG. 4 is a perspective view of an element of the adjustment means that is implemented inside the prostheses shown in FIGS. 1 to 3;

FIG. 5 is a perspective view of another element of adjustment means of the invention that is designed to co-operate with the element shown in FIG. 4;

FIG. 6 is a diagrammatic view from below, showing the adjustment possibilities offered by the adjustment means that are obtained by assembling together the elements shown in FIGS. 4 and 5;

FIG. 7 is a side view in section of the portion of prosthesis shown in FIGS. 1 and 2; and FIG. 8 is a front view of the assembly of the adjustment means shown in FIGS. 4 and 5.

DETAILED DESCRIPTION

The ankle prosthesis 1 of the present invention is designed to restore mobility at least in part to an ankle joint in a patient who has, for example, suffered disease or injury.

The ankle prosthesis 1 of the present invention can also be used to replace a previously implanted ankle prosthesis.

The ankle prosthesis 1 of the present invention comprises a talar implant 2 designed to be implanted in or on the talus (anklebone) 3, a tibial implant 4 designed to be implanted in or on the tibia 5, and an intermediate implant 6 designed to be interposed between the tibial implant 4 and the talar implant 2.

The intermediate implant 6 is designed to be mounted to move relative to the talar implant 2 in order to impart mobility to the ankle.

To this end, the intermediate implant 6 preferably has a contact surface 6A that is designed to come to bear against a surface 2A of the talar implant 2 that is of complementary shape, so that the intermediate implant 6 can move by sliding, with friction, relative to the talar implant 2.

In particularly preferable manner, as is shown in FIGS. 1 and 3, the contact surfaces 2A and 6A are rounded in shape, e.g., substantially spherically, cylindrically or frustoconically rounded, so as to form a contact interface 7 that allows the foot to move in plantar flexion and in dorsal flexion relative to the leg.

The intermediate implant 6 can, in particular, be made of polyethylene.

Advantageously, the prosthesis 1 of the invention also includes embedded adjustment means 10 that make it possible to modify the assembly configuration of the intermediate implant 6 relative to the tibial implant 4.

For this purpose, said adjustment means 10 are designed to alternate between a releasing state, in which they allow the intermediate implant 6 to move relative to the tibial implant 4 with at least first and second degrees of freedom that are distinct from each other, so as to make it possible to set the intermediate implant 6 relative to the tibial implant 4 in a chosen assembly configuration by using said first and second degrees of freedom, and a locking state in which they inhibit said first and second degrees of freedom so as to hold the prosthesis, and more particularly the intermediate implant 6 relative to the tibial implant 4, in the chosen assembly configuration.

Advantageously, the adjustment means 10 of the invention enable the practitioner to act on the prosthesis to select that arrangement of the intermediate implant 6 relative to the tibial implant 4 that the practitioner deems most appropriate for the anatomy of the patient, for each specific case and from among a plurality of potential configurations.

In the meaning of the invention, the term "embedded" is used to indicate that the adjustment means 10 are incorporated in the prosthesis 1 and that they intrinsically have arrangement variability that allows said prosthesis to be reconfigured. Advantageously, such incorporated and self-contained means make it possible, to a certain extent, to avoid the waste of time and of raw material that is inherent to using batches of interchangeable implants that are of various shapes and sizes, and that are designed to be implanted one after another until a satisfactory configuration is obtained.

Preferably, with the prosthesis 1 extending from the talar implant 2 to the tibial implant 4 along a mean extension axis (ZZ'), the first degree of movement corresponds substantially to a movement in translation that is transverse to said mean extension axis (ZZ'), and the second degree of freedom corresponds substantially to a movement in rotation about said mean extension axis (ZZ').

Preferably, when the prosthesis is implanted, said mean extension axis (ZZ') substantially coincides with the medullary axis of the tibia 5. In a healthy ankle joint, the leg tends to pivot about said medullary axis (ZZ') horizontally, through a yaw angle, relative to the foot, while said foot remains stationary on a flat floor.

More particularly, the transverse movement in translation corresponding to the first degree of freedom can advantageously take place substantially parallel to the anteroposterior translation axis (XX') that corresponds to a natural forwards or backwards movement of the leg and of the tibia relative to the foot while said foot remains stationary, or indeed it can take place substantially parallel to the mediolateral translation axis (YY') that corresponds to a sideways movement of the leg when said leg-tends to move laterally inwards towards the patient's other leg or outwards away therefrom while the foot remains stationary, or finally it can take place in a combination of such movements in translation.

However, in particularly preferable manner, the adjustment means 10 are arranged such that the first degree of freedom substantially coincides with the natural anteroposterior translation axis (XX').

Advantageously, the adjustment means 10 of the invention can thus make it possible to adjust the position of the intermediate implant 6 relative to the tibial implant 4 both linearly, in anteroposterior translation, in mediolateral translation, or in a combination of those two movements in translation, and angularly, through a yaw angle, in a wide variety of possible configurations.

Such a capacity for adjustment advantageously makes it possible to cause the axes of the prosthesis to coincide with the anatomical natural axes of the patient's ankle, and more particularly to position the intermediate implant 6 in a "neutral configuration" that is substantially centered on a point of origin Po about which the natural movements in anteroposterior translation, in mediolateral translation, and in rotation through a yaw angle normally take place, said point of origin Po substantially corresponding to the point of intersection between the axes (XX'), (YY'), and (ZZ').

Advantageously, when the intermediate implant 6 is in said neutral configuration, the stresses that are exerted on it, in particular while walking, are minimized and the comfort of the patient is optimized.

In particularly advantageous manner, while the adjustment means 10 are in their releasing state, they allow the intermediate implant 6 to move relative to the tibial implant 4 independently in each of the first and second degrees of freedom.

Thus, it is possible to modify independently firstly the linear position and secondly the angular position of said intermediate implant 6, in successive or simultaneous manner, and preferably continuously, i.e. without being limited to determined increment steps.

Once the practitioner has identified the configuration of the intermediate implant 6 that corresponds to the anatomy of the patient, and, more particularly, once the practitioner has positioned said intermediate implant 6 in the neutral configuration, the adjustment means 10 of the invention make it possible, when they go into the locking state, for the practitioner to remove the first and second degrees of freedom in order to lock said intermediate implant 6 relative to the tibial implant 4 in the selected position, i.e. in the chosen assembly configuration.

Naturally, it is quite possible, without going beyond the ambit of the invention, for the adjustment means 10 to inhibit and to release alternately a larger number of degrees of freedom, and in particular three degrees of freedom allowing a movement in rotation through a yaw angle and two transverse movements in translation along the anteroposterior axis (XX') and along the mediolateral axis (YY').

According to a major characteristic of the invention, the adjustment means 10 are placed under the control of control means 11 that are designed to be operable while the prosthesis 1 is in the assembled state in vivo, so as to cause said adjustment means 10 to alternate between their releasing state and their locking state, and vice versa.

Thus, in particularly advantageous manner, the ankle prosthesis 1 of the invention can be freely configured and locked in its functional configuration once it is already fully implanted in the joint, since the control means 11 remain accessible and can be actuated at any time, even though the talar implant 2, the intermediate implant 6, and the tibial implant 4 are stacked up in contact with one another in the joint space.

Thus, not only is the prosthesis of the invention extremely versatile due to the wide variety of assembly configurations that are accessible via its adjustment means 10, but also said prosthesis is extremely simple to put into place and to adjust in situ, thereby advantageously making it possible to obviate the need to use test prosthesis implants, and in particular to obviate the need to insert such implants into the joint space and to extract them therefrom in succession, because final adjustment can be enabled, obtained, maintained, or indeed subsequently modified, directly by combined use of the adjustment means 10 and of the control means 11 that are specific to the invention, and -that are-advantageously embedded-in the-fin-al prosthesis and -parts of-said prosthesis itself.

Advantageously, the control means 11 are of the "all or nothing" type so that they can either release or inhibit the first and second degrees of freedom simultaneously, and thus respectively impart adjustment capacity to the adjustment means 10 in full or completely remove that capacity therefrom.

Preferably, as is shown, in particular in FIGS. 1, 6, 7, and 8, the adjustment means 10 include an angularly positionable plate 12 associated with the intermediate implant 6, and engaged to slide and to move in rotation in a guide member 14 associated with the tibial implant 4, said guide member 14 being possibly integral with the tibial implant 4 or otherwise fastened to said tibial implant, for example by screw-fastening.

Advantageously, the, plate 12 is arranged such that the sliding takes place along a translation axis corresponding to the first degree of freedom, preferably in anteroposterior translation, while the movement in rotation corresponds to the second degree of freedom through a yaw angle about the mean extension axis (ZZ').

For this purpose, the plate 12 can advantageously be in planar-type contact with the tibial implant 4, and more particularly with the bottom main guiding face 14A of the guide member 14, which face 14A preferably coincides with the bottom face of said tibial implant.

Preferably, this contact plane is substantially parallel to the horizontal plane formed by the anteroposterior translation axis (XX') and by the mediolateral translation axis (YY'), and in particularly preferential manner, said contact plane coincides with said horizontal plane.

Preferably, the intermediate implant 6 is mounted on the plate 12, said plate having a base 15 for this purpose, which base 15 makes it possible to secure the intermediate implant 6 to the plate 12, thus disabling any relative movement of said intermediate implant with respect to said base.

This coupling can be achieved, for example, by interfitting, clipping, screw-fastening, or by any other equivalent means.

Naturally, in a variant embodiment, the plate 12 can also be formed integrally with the intermediate implant 6 in order to form a sort of one-piece block.

Preferably, the guide member 14 is provided with at least one rail 16 that obstructs the lateral movement of the plate 12 while allowing said plate 12 to move along an anteroposterior axis (XX').

Advantageously, in terms of movement, such a rail 16 forms an abutment that removes a degree of freedom in mediolateral translation, so as to allow only two degrees of freedom to remain from among the three degrees of freedom allowed by the smooth planar abutment coupling provided between the plate 12 and the guide member 14, the degrees of freedom that remain thus corresponding to movement in anteroposterior translation and to movement in rotation through a yaw angle.

Naturally, such a rail 16 can be obtained by various mechanical means, provided firstly that said means hold the plate 12 against the guide member 14 in order to prevent those elements from coming apart along the mean extension axis (ZZ') and secondly that said means impart the necessary degrees of freedom to the resulting coupling.

Thus, in a variant embodiment (not shown), it would be possible, for example, for the guide member 14 to include, projecting from its bottom main guiding face 14A, one or more broad-headed studs, e.g. formed by screws or rivets, disposed substantially parallel to the mean extension axis (ZZ'), the plate 12 being provided with oblong holes through which said studs pass.

Thus, the plate 12 would find itself retained between the heads of said studs and the bottom main guiding face 14A, the broad heads of the studs preventing said plate 12 from being dislocated along the mean extension axis (ZZ') while the oblong holes would be of length and of width greater than the width of the bodies of said studs, and would therefore present sufficient clearance relative to said studs to allow the plate to move linearly, in translation preferably at least along the anteroposterior axis (XX'), and angularly, in yaw angle, relative to the guide member 14.

However, in a preferred variant embodiment corresponding to the figures, the rail 16 is formed by an elongate trough that projects from the bottom main guiding face 14A of the guide member 14, here downwards, and that is preferably formed integrally therewith.

More particularly, said trough can be made up of two branches arranged in an L-shaped configuration, namely a first branch 16A that is substantially vertical and a second branch 16B that is substantially horizontal and that is folded over towards the plate 12, and preferably towards the centre of the guide member 14, in a plane that is substantially parallel to the bottom main guiding face 14A of said guide member 14, and to the plane formed by the anteroposterior translation axis XX' and by the mediolateral translation axis (YY').

Preferably, and as shown in FIGS. 1, 5, 6, and 8, the guide member 14 has at least two rails 16 that are substantially identical and that are disposed facing each other in order to support the plate 12 via its side edges 12A, 12B.

Preferably, the rails 16 are substantially rectilinear. Further, they preferably extend parallel to each other, and parallel to the anteroposterior translation axis (XX') so as to form, overall, a T-shaped groove into which the plate 12 is inserted. Preferably, said rails 16 and more generally the guide member 14 are formed integrally with the tibial implant 4, substantially in register with the side edges thereof.

Advantageously, such a lateral arrangement of the rails 16 enables the plate 12 to be engaged between said rails and therefore held stably and rigidly and guided accurately and smoothly substantially on either sides, while its position relative to the tibial implant 4, and thus the position of the intermediate implant 6 supported by said plate 12, is being adjusted.

Preferably, the rail or each of the rails 16 has a support portion 17 that is arranged to project towards the plate 12 in order to support said plate, and disengagement portions 18 that are disposed on either side of the support portion 17 and that are arranged to be set back from said plate 12. Advantageously, the support portion 17 corresponds to the horizontal branch 16B of the trough that forms the rail 16 and that forms a vertical abutment supporting the plate 12.

Thus, as is shown in particular in FIGS. 5 and 6, in a plane that is normal to the mean extension axis (ZZ'), each rail 16 has an outline with an undulation preferably having a central projection that corresponds to the support portion 17 and that is designed to come to be placed under the side edges of the base 12, said central projection being flanked on either side, and more particularly at the anterior and at the posterior ends of the rail 16, by disengagement portions 18 forming setbacks or recesses that are advantageously arranged to enable said plate 12 to pivot through a yaw angle without coming into abutment against the horizontal branch 16B of the rails 16, thereby maximizing the amplitude of adjustment of the movement through the yaw angle a.

Advantageously, the support portion 17 of each rail is thus limited to the bearing surface of area just necessary and sufficient for holding and guiding the plate 12, and does not hinder the movements in rotation for adjusting said plate relative to the tibial implant 4.

Naturally, the person skilled in the art can adapt the length of said support portion 17, and thus the length of said bearing surface as a function of the stroke that it allows the plate 12 to travel.

By way of example, the length, as measured along the anteroposterior translation axis (XX') of each of the disengagement portions 18 and of the support portion 17 can be substantially the same, and substantially equal to one third of the total length of the rail 16, the support portion thus extending substantially in the middle of said rail.

It is also possible for the support portions 17 to be offset, e.g. forwards, relative to the middle of the rail.

At its side edges 12A, 12B, the plate 12 is preferably provided with projecting and curved carrier tongues 20 that are arranged to co-operate pivotally and slidingly with their respective rails 16.

More particularly, said carrier tongues 20 thus form lugs, each of which is designed to be inserted into a respective rail 16, and more particularly to come to be received freely in the gap 16l formed between the bottom main guiding face 14A of the tibial implant 4 and the top face of the support portion 17.

Advantageously, the plate is thus retained in translation along the medullary axis (ZZ') by the support portions 17, while the carrier tongues 20 come laterally into abutment against the end-walls of the grooves, over two substantially linear contact zones corresponding to the thickness of said tongues, i.e. against the inside vertical walls 16A of the rails 16. Such an arrangement guarantees that the plate 12 is put into abutment on either side along the mediolateral axis (YY'), and therefore that it is held stationary along said mediolateral axis, while also, by means of the curvature of said carrier tongues, allowing the freedom of movement through a yaw angle to take place about the medullary axis, and further through a translation along the anteroposterior axis (XX').

Thus, the same members, namely the carrier tongues 20, simultaneously perform a plurality of functions, namely a mechanical retaining function both along the medullary axis (ZZ') and along the mediolateral axis (YY'), and two mobility functions allowing mobility in anteroposterior translation, by sliding, and through a yaw angle, by pivoting.

Naturally, without going beyond the ambit of the invention, it may be possible to obtain a similar result by providing the prosthesis 1 with a plurality of distinct guide members 14 that are arranged one above the other, one guide member allowing the movement in anteroposterior translation to take place and the other member allowing the movement in rotation through a yaw angle to take place.

However, the preferred arrangement offers, in particular, the advantages of being extremely simple to make and to assemble, of being very compact, as far as a single stage of guide member 14 enables the movements both in rotation and translation, and of having excellent reliability in operation.

In particularly preferred manner, the opposite carrier tongues 20 correspond to portions of a common disk of radius R and of centre $\Omega$, said radius being chosen such that the diameter of the disk defined by the carrier tongues 20 substantially corresponds to the distance D measured between the rails 16.

Thus, by means of the very small amount of clearance between the outside walls of the carrier tongues 20 and the end-walls of the rails 16, accurate guidance is obtained in anteroposterior translation but also in rotation, allowing the pivoting through a yaw angle to take place with almost no transverse movement in mediolateral translation.

In a particularly preferred variant embodiment corresponding in particular to FIGS. 1 to 4, the plate 12 has a base 15 that is connected to the intermediate implant 6 and that underlies a coupling slab 21 that is substantially rectangular and plane in shape.

The base 15 is preferably separated from said coupling slab 21 by two side, preferably linear, grooves that form a neck of shape substantially complementary to the shapes of the support portions 17, thereby enabling the plate 12 to be engaged into the rails 16 from the front along the anteroposterior axis (XX').

Said coupling slab 21 preferably has an overall width that is less than the overall width of the base 15, and is extended laterally, at each of its two opposite side edges, by a respective carrier tongue 20 that advantageously has a substantially circularly arcuate outline that is substantially centered relative to said coupling slab 21. Preferably, the center Ω of the disk within which the tongues lie corresponds substantially to the center of the coupling slab 21.

Preferably, the coupling slab 21 is formed integrally with the base 15, so that the plate 12 forms a one-piece unit.

In addition, the thickness e of the coupling slab 21 is, in particular at the carrier tongues 20, substantially equal to the width of the gap 161 between the top face of each of the support portions 17 and the bottom face of the tibial implant 4, so as to enable the plate 12 to be inserted into the guide member 14 and to be slidably guided therein with a small amount of vertical clearance.

Advantageously, the layered structure of the plate 12 makes it possible to separate the guiding top portion of said plate 12, including the coupling slab 21, from the bottom portion including the base 15, and thus to possibly implement an enlarged base 15 with optimized width, so as to improve the stability of the intermediate implant 6 and more generally of the prosthesis 1.

In addition, the control means 11 preferably comprise at least one clamping member 25 that is suitable for pressing the intermediate implant 6 against the tibial implant 4, and more particularly for pressing the carrier tongues 20 of the plate 12 against the support portions 17 of the rails 16, in order to lock said implants relative to each other.

Advantageously, the clamping member 25 is reversible, thereby making it possible, in alternation, firstly to hold the plate 12 stationary by clamping it by friction, and secondly to release said plate so as to allow it to move with at least first and second degrees of freedom within the guide member 14.

In a particularly preferred manner, the control means 11, and more particularly the clamping members 25, are accessible from the front and directly on the anterior portion of the prosthesis, and more particularly at the shield 27 of the tibial implant 4.

In a preferred variant embodiment, as shown in FIG. 7, the clamping member(s) 25 is/are formed by one or more compression screws 26 that are preferably disposed slantwise in the tibial implant 4 and pointing towards the intermediate implant 6.

More particularly, said compression screws 26 can be constituted by cone-pointed set screws that pass through the tibial implant 4 from top to bottom, namely from the shield 27 to the bottom face of said tibial implant, which face coincides with the bottom main guiding face 14A of the guide member, the tips of which screws come through into abutment against the top face of the plate 12.

Preferably, the inclination of the insertion axis (SS') along which each of the compression screws 26 is inserted relative to the plane of contact between the plate 12 and the tibial implant 4, and the angle of taper of the conical or frustconical tips of said compression screws are chosen such that the wall of the tip of each of said screws comes into substantially flat abutment against the base 12, as shown in FIG. 7.

Advantageously, the through holes 30 forming access channels for the compression screws 26 that are provided in the tibial implant 4 are provided with thread 30' in the thick portion situated at the base of the shield 27, thereby making it possible to secure said compression screws 26 in a zone having a good thickness of material, and thus guaranteeing effective clamping, and therefore that the plate 12 is held stationary safely relative to the tibial implant 4.

In a variant embodiment corresponding to FIG. 3, the prosthesis 1 can include single control means 11, and, in this example, a single compression screw 26, substantially central relative to the tibial shield 27 and to the plate 12 on the mediolateral axis (YY').

The tibial shield 27 can then have two fastening orifices 28 on either side of said control means 11, those orifices being designed to pass screws making it possible to fasten the tibial implant 4 to the tibia 5.

However, in a preferred variant embodiment corresponding to FIGS. 1, 2, 5, and 8, the control means 11 comprise two clamping members 25, and more particularly two compression screws 26, disposed on either side of a single fastening orifice 28, in order to balance the clamping pressure better, substantially in register with the support portions 17 of the rails 16.

Advantageously, such a configuration makes it possible to secure the intermediate implant 6 to the tibial implant 4 particularly stably and safely, not only by distributing the stresses relatively uniformly, but also by duplicating the clamping members, thereby considerably limiting the risk of accidental unlocking.

In addition, the compression screws 26 can advantageously be locked, after being tightened, by means of check-screw 29.

Although it is possible for the compression screws 26 to act indirectly on the plate 12, e.g. via a chock or a compression pad, they preferably come into direct contact with said plate 12, as shown in FIG. 7, thereby making it possible to simplify tightening and to improve the quality of the clamping for holding the plate stationary.

Advantageously, the inclination of the compression screws 26 of the invention makes it possible to act remotely on the state of the adjustment means 10, from the shield 27 of the tibial implant 4 and through threaded channels 30 opening out in the bottom main guiding face 14A of the guide member.

Naturally, the clamping members 25 could be replaced with any type of means that are equivalent to compression screws 26, and in particular with ties working in traction rather than in compression, and making it possible, for example, to press the plate 12 upwardly against the bottom main guiding face 14A, or to bring the support portions 17 towards said bottom main guiding face 14A so as to clamp the carrier tongues 20. It could also be possible to consider using operable wedges inside the guide member 14 so as to lock the plate 12, said wedges being, for example, reversibly snap-fastened between the plate 12 and the bottom face of the tibial implant 4.

The invention can also be considered as relating to an ankle prosthesis comprising a talar implant 2, a tibial implant 4 and an intermediate implant 6 as set forth above, said intermediate implant 6 being designed to be mounted to move relative to said talar implant 2 in order to impart functional mobility to the ankle, and said intermediate implant 6 being mounted on the tibial implant 4 in a displaceable manner with a least a first degree of freedom, preferably in anteroposterior translation, and a second degree of freedom, preferably in rotation through a yaw angle, said prosthesis 1 further comprising a lock, namely at least one clamping member 25 such as a compression screw 26, for reversibly securing the intermediate implant 6 and the tibial implant 4 together in suppressing said first and second degrees of freedom, once a suitable assembly configuration is achieved, said lock being accessible from an apparent outer surface of the prosthesis, preferably the front surface of the tibial implant 4, said lock thus being operable in vivo, while the prosthesis is already functionally assembled in the joint.

In addition, it is remarkable that the prosthesis 1, and more particularly the tibial implant 4, can have a substantially asymmetrical structure, oriented differently depending on whether the prosthesis is designed for the right foot or for the left foot, the right prosthesis and the left prosthesis then being mirror images of each other about the sagittal plane of the patient.

Furthermore, the person skilled in the art can adapt adjustment means and control means of the invention to suit various types of joint prostheses, other than ankle prostheses.

Operation of the prosthesis of the invention is described in more detail below, in what can constitute an arthroplasty (joint replacement) surgical method of the invention.

The practitioner starts by making one or more incisions in order to access the joint and in order to prepare said joint, in particular by machining the tibia 5 and the talus 3.

The practitioner then mounts the talar implant 2 on the talus 3, and the tibial implant 4 on the tibia 5 by means of one or more fastening screws inserted via the fastening orifices 28.

Then, the practitioner fastens the intermediate implant 6 to the base 12, e.g. by fitting said implant into the base 15, and positions the resulting subassembly formed in the joint between tibial implant and the talar implant, by inserting the fastening slab 21 of the base 12 into the rails 16 from the front to the rear, substantially along the anteroposterior axis (XX'). Advantageously, the practitioner can access the guide member 14 from the anterior face of the prosthesis and of the joint.

Advantageously, the guide members 14 are provided with a back abutment 31 that prevents the plate 12 from being pushed too far under the tibial implant 4.

It is remarkable that the "final" prosthesis 1 can thus be globally implanted and assembled in vivo in the joint, and immediately includes all its functionally necessary components, prior to the adjusting operations.

Since the compression screws 26 are initially not engaged or at least not tightened, the base 12 and the intermediate implant 6 are free to move together in rotation through a yaw angle and in anteroposterior translation relative to the tibial implant 4.

As is shown in FIG. 6, the amplitude of these movements corresponds to the linear stroke d and to the angular movement α allowed by the geometrical and dimensional configuration of the guide member 14.

Advantageously, the base 12 can in particular move through a yaw angle until one of its side edges comes into abutment against the recess of the corresponding disengagement portion 18, and in particular said base can take up all of the intermediate positions between the two positions shown respectively in uninterrupted lines and in dashed lines in FIG. 6.

The practitioner then looks for the neutral position that corresponds to the movement of smallest amplitude and to minimum stress during walking.

For this purpose, it is remarkable that the practitioner can advantageously use the self-centering capacity possessed by the prosthesis of the invention.

It is possible for the practitioner to impart a succession of movements in dorsal flexion and in plantar flexion while the adjustment means 10 are in their releasing state, the intermediate implant 6 then being free to move between the tibial implant 4 and the talar implant 2 by using the first and second degrees of freedom allowed by said adjustment means 10, thereby, under the action exerted by the talar implant 12 on the intermediate implant 6 via the contact interface 7, iteratively and automatically centering said intermediate implant 6 substantially on the point of origin Po.

More particularly, the practitioner can thus adjust and select on one hand the angular position and on the other hand the linear position of the intermediate implant 6 with respect to the tibial implant 4, from among a range of various possible yaw angle directions and anteroposterior linear positions respectively.

The ergonomic arrangement of the prosthesis advantageously makes the implementation of said prosthesis into the suitable neutral assembly configuration particularly simple and quick.

Once the plate 12 and thus the intermediate implant 6 are correctly positioned relative to the tibial implant 4, the practitioner can lock them in position in vivo in the selected assembly configuration, by actuating the control means 11 and more particularly by tightening the compression screws 26 until they come to clamp the plate 12 by sandwiching it against the support portions 17 of the rails 16.

Advantageously, locking the intermediate implant 6 to the tibial implant 4 does not interfere with the adjusted angular and linear parameters, so that the proper assembly configuration is substantially "frozen" as selected.

Further, the control means 11 of the invention advantageously leave the surgeon free to cause the adjustment means 10 to alternate as often as desired between their releasing state, enabling the surgeon, in particular, to adjust the prosthesis by self-centering, and their locking state, in which said adjustment means 10 hold said prosthesis in the chosen configuration, and to do so even though the entire prosthesis remains implanted in vivo.

Thus, it is possible to achieve one or more successive adjustment operations of the intermediate implant 6 relative to the tibial implant 4 by simply loosening the clamping members 25 for releasing said intermediate implant, then positioning the intermediate implant 6 in rotation and/or translation, and (re-)locking the clamping members, without it being necessary to disassemble or extract the prosthesis 1 in part or as a whole, and without it being necessary to exchange or add any component thereof.

Once the prosthesis 1 is restrained in this way, i.e. once the adjustment means 10 are set in their locking state by the control means, said prosthesis advantageously retains functional mobility that, in this example, is preferably exclusively for pivoting between the intermediate implant 6 and the talar implant 2.

The prosthesis is thus ready for final use as such.

The practitioner can then close the incision and begin physiotherapy on the patient after the wound has healed.

It is remarkable that, insofar as the adjustment means 10 and the control means 11 are implanted permanently with the prosthesis 1, they advantageously remain available and operational for subsequent action.

It is thus possible to consider successively per- or postoperatively changing the adjustment of the neutral configuration in vivo, or indeed subsequently releasing the degrees of freedom that are initially inhibited by the control means 11.

Thus, the prosthesis of the invention makes it possible, by means of a particularly simple, robust, and compact structure, to customize the treatment of each patient by adapting to accommodate not only the anatomic configuration but also the state of the joint of said patient, and to do so without requiring any extra work or equipment related to prior implementation of configuration testing by means of non-final implants.

SUSCEPTIBILITY OF INDUSTRIAL APPLICATION

The invention finds its industrial application in designing and manufacturing joint prostheses, in particular ankle prostheses.

The invention claimed is:

1. An ankle prosthesis comprising:
    a talar implant;
    a tibial implant;
    an intermediate implant designed to be interposed between the tibial implant and the talar implant, the intermediate implant being designed to be mounted to move relative to the talar implant in order to impart mobility to an ankle; and
    embedded adjustment means for modifying an assembly configuration of the intermediate implant relative to the tibial implant, the adjustment means alternatable between a releasing state, in which they allow the intermediate implant to move relative to the tibial implant with at least first and second degrees of freedom that are distinct from each other, and a locking state, in which they inhibit the first and second degrees of freedom so as to hold the prosthesis in the chosen assembly configuration;
    wherein the adjustment means are placed under control of control means that are accessibly disposed along an anteroposterior axis and are operable while the prosthesis is in the assembled state in vivo, so as to cause the adjustment means to alternate between their releasing state and their locking state.

2. The ankle prosthesis according to claim 1, wherein with the prosthesis extending from the talar implant to the tibial implant along a mean extension axis, the first degree of freedom corresponds substantially to a movement in translation transverse to the mean extension axis and the second degree of freedom corresponds substantially to a movement in rotation about the mean extension axis.

3. The ankle prosthesis according to claim 1, wherein the adjustment means comprise an angularly positionable plate associated with the intermediate implant and engaged to slide and to move in rotation in a guide member associated with the tibial implant.

4. The ankle prosthesis according to claim 3, wherein the guide member comprises at least one rail that obstructs lateral movement of the plate while allowing the plate to move along the anteroposterior axis.

5. The ankle prosthesis according to claim 4, wherein the guide member comprises at least two rails disposed facing each other in order to support the plate via its side edges.

6. The ankle prosthesis according to claim 4, wherein each of the at least one rail comprises rails has a support portion arranged to project towards the plate in order to support the plate, and disengagement portions disposed on either side of the support portion and arranged to be set back from the plate.

7. The ankle prosthesis according to claim 5, wherein, at the side edges, the plate is provided with projecting and curved carrier tongues that co-operate pivotally and slidingly with their respective rails.

8. The ankle prosthesis according to claim 7, wherein the plate comprises a base that is connected to the intermediate implant and that lies under a coupling slab of substantially rectangular and planar shape, and from which it is separated by two grooves enabling the plate to be engaged in the rails, the coupling slab having an overall width that is less than an overall width of the base, and being extended laterally, at each of its two opposite side edges, by a respective carrier tongue that advantageously has a substantially circularly arcuate outline that is substantially centered relative to the coupling slab.

9. The ankle prosthesis according to claim 1, wherein the control means comprise at least one clamping member suitable for pressing the intermediate implant against the tibial implant in order to lock the implants relative to each other.

10. The ankle prosthesis according to claim 9, wherein the at least one clamping member is formed by one or more compression screws disposed slantwise in the tibial implant and pointing towards the intermediate implant.

11. An ankle prosthesis comprising:
    a talar implant;
    a tibial implant;
    an intermediate implant designed to be interposed between the tibial implant and the talar implant, the intermediate implant being designed to be mounted to move relative to the talar implant in order to impart mobility to an ankle; and
    an adjustment means for modifying an assembly configuration of the intermediate implant relative to the tibial implant, the adjustment means alternatable between a releasing state, in which they allow the intermediate implant to move relative to the tibial implant with at least one of a first and second degrees of freedom that are distinct from each other, and a locking state, in which they inhibit the at least one of the first and second degrees of freedom so as to hold the prosthesis in the chosen assembly configuration;
    wherein the adjustment means are placed under control of control means that are accessibly disposed along an anteroposterior axis and are operable while the prosthesis is in the assembled state in vivo, so as to cause the adjustment means to alternate between their releasing state and their locking state.

12. An ankle prosthesis comprising:
    a talar implant;
    a tibial implant;
    an intermediate implant interposed between the tibial implant and the talar implant, the intermediate implant being mounted to move relative to the talar implant in order to impart mobility to an ankle, the intermediate implant and the tibial implant having an assembly configuration, the assembly configuration having a releasing state, in which the intermediate implant moves relative to the tibial implant with at least one of a first and second degrees of freedom that are distinct from each other, and a locking state, in which the intermediate implant is locked relative to the tibial implant to inhibit movement of the intermediate implant relative to the tibial implant with respect to the at least one of the first and second degrees of freedoms;
    at least one member that presses the intermediate implant against the tibial implant to cause the intermediate implant and tibia component to alternate between the releasing state and the locking state, the at least one member being accessibly disposed along an anteroposterior axis and operable while the ankle prosthesis is in an assembled state in vivo.

13. An ankle prosthesis comprising:
a talar implant;
a tibial implant;
an intermediate implant interposed between the tibial implant and the talar implant, the intermediate implant being mounted to move relative to the talar implant in order to impart mobility to an ankle;
means for modifying an assembly configuration of the intermediate implant relative to the tibial implant, the assembly configuration having a releasing state, in which the intermediate implant moves relative to the tibial implant with at least one of a first and second degrees of freedom that are distinct from each other, and a locking state, that inhibits movement the intermediate implant relative to the tibial implant with respect to the, at least one of the, first and second degrees of freedom; and
means for controlling the means of modifying, the means for controlling being accessibly disposed along an anteroposterior axis and operable while the prosthesis is in an assembled state in vivo.

14. A method of providing an ankle prosthesis, the method comprising:
mounting a talar implant on a talus;
mounting a tibial implant on a tibia;
fastening an intermediate implant to the tibial implant;
adjusting in vivo a relative position between the tibial implant and the intermediate implant about, at least, a first degree of freedom and a second degree of freedom, which is distinct from the first degree of freedom; and
locking in vivo along an anteroposterior axis a selected position between the tibial implant and the intermediate implant.

15. The method of claim 14, wherein the adjusting in vivo a relative position between the tibial implant and the intermediate implant about, at least a first degree of freedom and a second degree of freedom, which is distinct from the first degree of freedom further comprises: allowing a movement in, at least one of, rotation through a yaw angle, translation along the anteroposterior axis, and translation along a mediolateral axis.

16. The method of claim 14, wherein the fastening an intermediate implant to the tibial implant, further comprises:
securing the intermediate implant to an angularly positional plate, and
coupling the angularly positional plate to the tibial implant.

17. A method of providing an ankle prosthesis, the method comprising:
mounting a talar implant on a talus;
mounting a tibial implant on a tibia;
locating an intermediate implant between the talar implant and the tibial implant;
adjusting in vivo a relative position between the tibial implant and the intermediate implant about, at least, a first degree of freedom and a second degree of freedom, which is distinct from the first degree of freedom; and
locking in vivo along an anteroposterior axis a selected position between the tibial implant and the intermediate implant.

18. The method of claim 17, wherein the adjusting in vivo a relative position between the tibial implant and the intermediate implant about, at least a first degree of freedom and a second degree of freedom, which is distinct from the first degree of freedom, further comprises:
utilizing an adjustment means implanted with the ankle prosthesis.

19. The method of claims 18, wherein the locking in vivo along an anteroposterior axis a selected position between the tibial implant and the intermediate implant, further comprises:
utilizing a control means implanted with the ankle prosthesis.

20. The method of claim 19, wherein the utilizing an adjustment means implanted with the ankle prosthesis, further comprises:
allowing a movement in, at least one of, rotation through a yaw angle and translation along the anteroposterior axis.

21. The method of claim 17, wherein the adjusting in vivo a relative position between the tibial implant and the intermediate implant about, at least a first degree of freedom and a second degree of freedom, which is distinct from the first degree of freedom, comprises:
allowing a movement in rotation through a yaw angle.

22. The method of claim 17, wherein the adjusting in vivo a relative position between the tibial implant and the intermediate implant about, at least a first degree of freedom and a second degree of freedom, which is distinct from the first degree of freedom, comprises:
allowing a movement in translation along, at least one of, the anteroposterior axis and a mediolateral axis.

* * * * *